Aug. 23, 1932. E. H. MANN Plant Pat. 21
CERISE ROSE
Filed Feb. 29, 1932
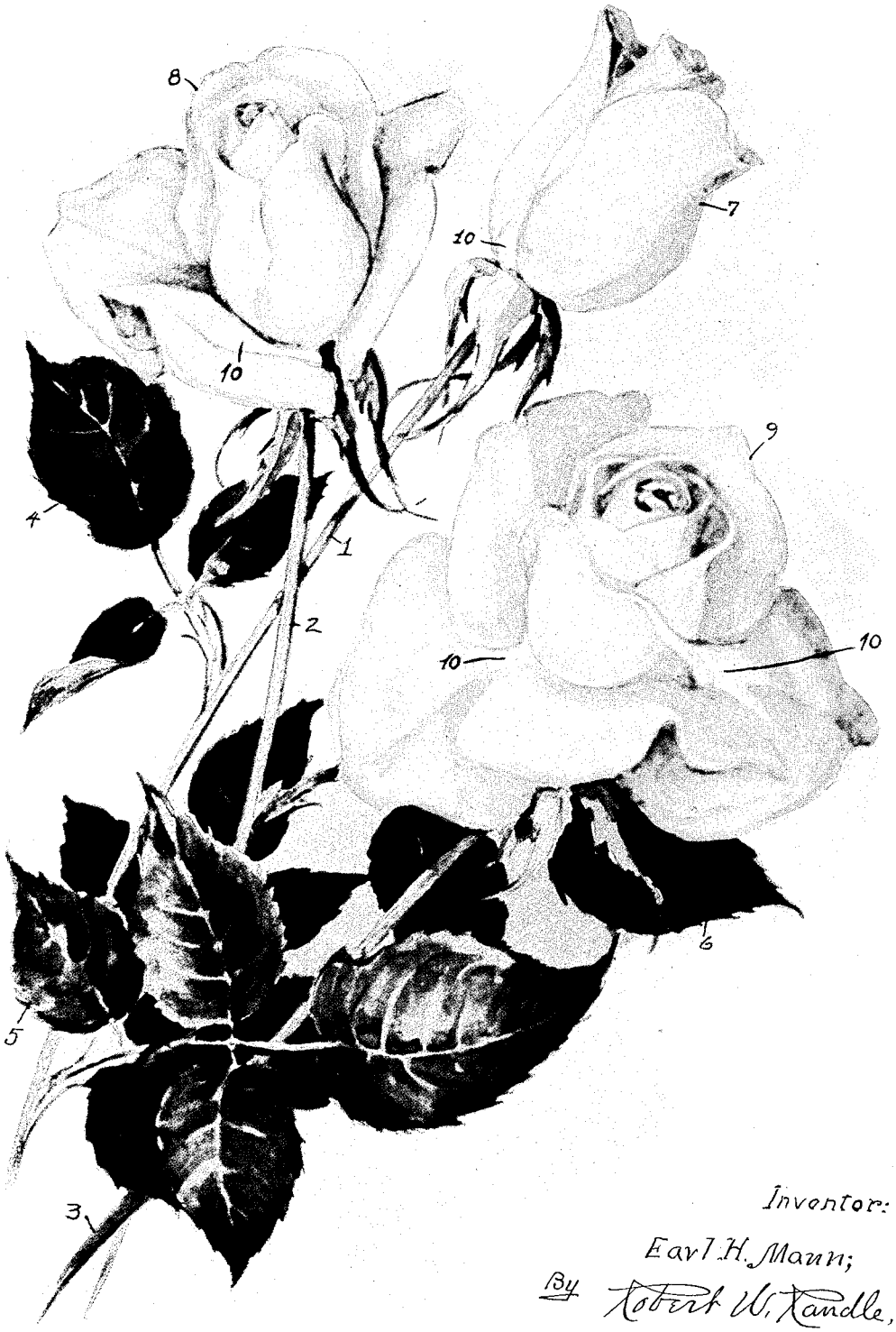
Inventor:
Earl H. Mann;
By Robert W. Randle,
Attorney.

Patented Aug. 23, 1932

Plant Pat. 21

UNITED STATES PATENT OFFICE

EARL H. MANN, OF RICHMOND, INDIANA, ASSIGNOR TO E. G. HILL COMPANY, OF RICHMOND, INDIANA, A CORPORATION OF INDIANA

CERISE ROSE

Application filed February 29, 1932. Serial No. 595,876.

This invention relates to the production of a new and distinct variety of rose, which is asexually produced, which is unique in its characteristics, highly pleasing in its appearance, and in which its new features have been permanently fixed, whereby it may be continuously reproduced without danger of retrogradation.

Broadly speaking, I have, as one of my objects, the production of an entirely new variety of rose which has many outstanding valuable and distinctive features, which I will hereinafter more fully particularize in concrete detail.

More specifically stated, the objects which I have attained, in this instance, and which are involved in my new rose, is the production of an entirely new and distinct variety of rose, the same being easily recognizable by its deep cerise pink bloom, with a yellow base at its petals; its large and pointed buds; producing a sweet scented spicy fragrance heretofore unknown in roses; its large and artistic petals, eventuating in long pointed buds of very large size; which is exceptionally prolific in its production of fully developed bloom; and the entire plant being of very strong vigorous upright and compact growth.

Other objects and especial advantage of my new rose will suggest themselves to the rosarian in the course of the following detailed description, and that which is new and useful will be correlated in the appended claim.

A picturization of my new rose is shown in the accompanying painting, forming a part of this specification, wherein is clearly visualized my new rose in its natural colors, and showing other new and novel features which I have developed therein.

In the painting, numerals 1, 2 and 3 designate the stems.

Numerals 4, 5 and 6 designate the leaves, which are associated with the bloom and are attached to said stems.

Numeral 7 designates a bud which is just starting to open out.

Numeral 8 designates a partly developed bloom.

And numeral 9 designates a full blown rose, fully developed.

My new rose was produced from a rose seedling, of an unnamed variety, which I employed as the male member, and a rose of the butterfly variety, which I employed as the female member. From the stamens of the male member pollen was taken and injected into the stigma of the female member. As a result of this fecundation fertile seeds were formed in the stigmas of the female member, which seed were sown in properly prepared soil, which seeds germinated and brought forth plants which produced both male and female roses. When the said male and female roses were fully open in bloom, that is when they were ripe, then the pollen from the stamens of the male members was at the proper time placed in the stigmas of the female members, thereby crossing the two, therefore after germination they produced my new rose, which is therefore a hybrid tea rose. My new rose was then asexually reproduced and carefully propagated, and it has been further greatly improved by intercrossing and otherwise, whereby its new and desirable characteristics have been fixed, whereby it can now be cultivated and grown without danger of its reverting.

The bloom of my new rose is especially noticeable by reason of its deep pink brilliant cerise colorature throughout its petals, except at the base the petals show as yellow, as indicated in the painting by the numeral 10.

My rose is further characterized by reason of its extra large, long, and pointed buds, which are unusually well formed, whereby when in full bloom the rose produces a very attractive and artistic appearance.

The stems of my rose plant are very long, and are unusually strong and are vigorous in growth, and they naturally grow upright and compact. My new rose is highly prolific in its production of fully developed bloom. And, finally, my new rose is highly fragrant, dispensing a sweet scented spicy odor, which adds greatly to its many attractive features.

Having now fully shown and described my new rose, together with its origin, and the manner of its production, what I claim and desire to secure by Letters Patent of the United States, is—

The rose herein shown and described, characterized by its deep cerise pink bloom, with a yellow base at its petals, its large and pointed buds, its sweet scented spicy fragrance, its long and strong stem, and its prolific production of blooms.

EARL H. MANN.